United States Patent [19]

Mitchell

[11] Patent Number: 4,561,062
[45] Date of Patent: Dec. 24, 1985

[54] STRESS MEASUREMENT BY X-RAY DIFFRACTOMETRY

[75] Inventor: Crighton M. Mitchell, Kanata, Canada

[73] Assignee: Her Majesty the Queen in right of Canada, as represented by the Minister of Energy, Mines and Resources Canada, Ottawa, Canada

[21] Appl. No.: 467,955
[22] Filed: Feb. 18, 1983
[51] Int. Cl.[4] ................... G01N 15/00; G01M 5/00
[52] U.S. Cl. ............................. 364/555; 73/786; 364/508; 378/72
[58] Field of Search ............... 364/508, 555; 378/71, 378/72; 250/307; 73/786, 787

[56] References Cited

U.S. PATENT DOCUMENTS

| | | | |
|---|---|---|---|
| 2,184,174 | 12/1939 | Bertram | 250/65 |
| 2,462,374 | 2/1949 | Firth | 250/83.6 |
| 2,898,470 | 8/1959 | Khol | 250/53 |
| 3,023,311 | 2/1962 | Bessen | 250/51.5 |
| 3,030,507 | 4/1962 | Khol | 250/51.5 |
| 3,197,638 | 7/1965 | Sinclair | 250/83.3 |
| 3,402,291 | 9/1968 | Weinman | 250/51.5 |
| 3,411,001 | 11/1968 | Wilchinsky | 250/51.5 |
| 3,483,377 | 12/1969 | Borkowski | 250/83.3 |
| 3,614,425 | 10/1971 | Yoshimatsu | 250/51.5 |
| 3,617,705 | 11/1971 | Takano | 250/51.5 |
| 3,634,686 | 1/1972 | Sekita | 250/51.5 |
| 3,639,758 | 2/1972 | Shimura | 250/51.5 |
| 3,639,760 | 2/1972 | Mizunuma | 250/51.5 |
| 3,868,506 | 2/1975 | Ogiso | 250/278 |
| 3,934,138 | 1/1976 | Bens | 250/278 |
| 4,042,825 | 8/1977 | Ruud | 250/272 |
| 4,076,981 | 2/1978 | Sparks et al. | 250/272 |
| 4,095,103 | 6/1978 | Cohen et al. | 250/277 |
| 4,125,771 | 11/1978 | Erwin | 250/277 |
| 4,128,762 | 12/1978 | Nagao et al. | 250/272 |
| 4,247,771 | 1/1981 | Frevel | 250/273 |
| 4,287,416 | 9/1981 | Kramer et al. | 250/273 |
| 4,476,386 | 10/1984 | Reid et al. | 250/307 X |

FOREIGN PATENT DOCUMENTS

| | | |
|---|---|---|
| 3119287 | 3/1982 | Fed. Rep. of Germany . |
| 2007479 | 5/1979 | United Kingdom . |
| 1585608 | 3/1981 | United Kingdom . |
| 441490 | 9/1972 | U.S.S.R. . |
| 624150 | 2/1977 | U.S.S.R. . |
| 737818 | 12/1977 | U.S.S.R. . |

OTHER PUBLICATIONS

Jrl. of Metals, "Review of Nondestructive Methods for Residual Stress Measurement", Jul. 1981, C. O. Ruud, pp. 35–39.
Advances in X-Ray Analysis, vol. 20 (1977), "A Dual Detector Diffractometer for Measurement of Residual Stress", C. M. Mitchel, pp. 379–391.
Advances in X-Ray Analysis, vol. 22 (1979), "New Method for Fast XRPD using a Position Sensitive Detector", H. E. Göbel, pp. 255–265.

*Primary Examiner*—Errol A. Krass
*Assistant Examiner*—Kevin J. Teska

[57] ABSTRACT

A portable X-ray diffractometer for measurement of residual stress in metallic specimens, especially large structures, such as bridges, pipelines etc. The instrument consists of a pair of position sensitive detectors arranged to be mounted in fixed positions relative to the specimen. An X-ray source that projects a collimated incident beam onto the area of the specimen under examination is located between the detectors so that each receives a diffraction line. The source is scanned stepwise in an arc about the specimen area, while the specimen and both the detectors remain fixed. The diffraction lines received in each detector are stored in a computer as histograms of intensity values. For each angular relationship between the incident beam and the chosen direction of strain measurement, a series of such intensity values corresponding to a given diffraction angle for successive diffraction lines is averaged and a resultant diffraction line obtained for each detector. To keep the mean strain directions constant and achieve a constant range of grain orientations for all diffraction angles, the instrument restricts the intensity values so averaged to those that fall within a virtual window. This window is moved along the channels, one or more channels per scanning step. The two resultant series of averaged values are examined to find peaks or other characteristics of the diffraction line and the angular relationships corresponding thereto. This knowledge enables determination of lattice strains in two directions, the two strains determining the stress in the specimen surface.

19 Claims, 16 Drawing Figures

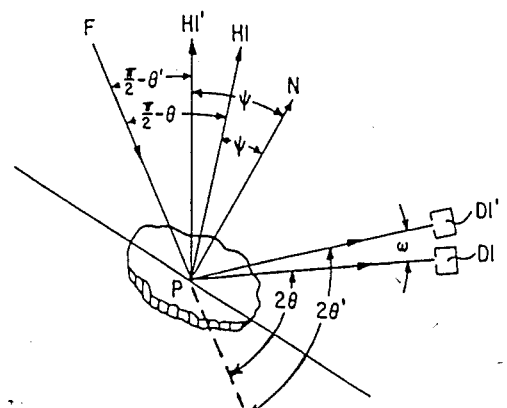
FIG. 2A PRIOR ART COUNTER DIFFRACTOMETER
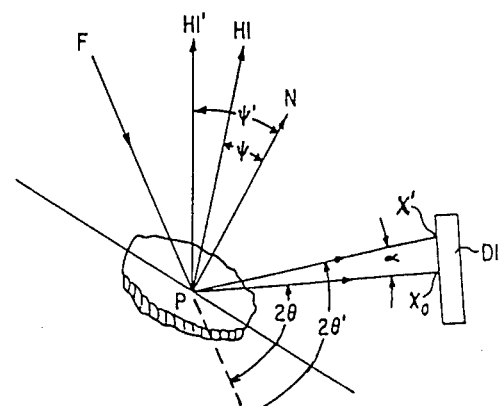
FIG. 2B PRIOR ART POSITION SENSITIVE DETECTOR DIFFRACTOMETER

STRESS MEASUREMENT BY X-RAY DIFFRACTOMETRY

FIELD OF THE INVENTION

This invention relates to X-ray diffractometry and more particularly to apparatus and methods for the measurement of residual stress in polycrystalline, e.g. metallic, specimens.

The procedure is based on measurement of the lattice strain of crystals by X-ray diffraction, in which change in the interplanar spacing of a set of crystal lattice planes due to strain causes a change in the diffraction angle of the scattered X-ray beam, from which latter change the magnitude of the strain can be determined. In a polycrystalline specimen, from well known relations for elastic behaviour in isotropic materials, the stress on a plane normal to a given direction in the surface has a component in the given direction which can be calculated from measurement of lattice strain in two directions in a plane containing the given direction and the normal to the specimen surface. In general three such stress components in three directions in the surface are required to determine the principal stresses and thus express the state of stress in the surface.

BRIEF DESCRIPTION OF THE DRAWINGS

To enable the background to the invention and the specific prior art to be described with the aid of diagrams, the figures of the accompanying drawings will first be listed.

FIGS. 1A, 1B, 2A and 2B are diagrams showing the basic considerations in an X-ray diffractometer.

BACKGROUND TO THE INVENTION

Figure 1A:
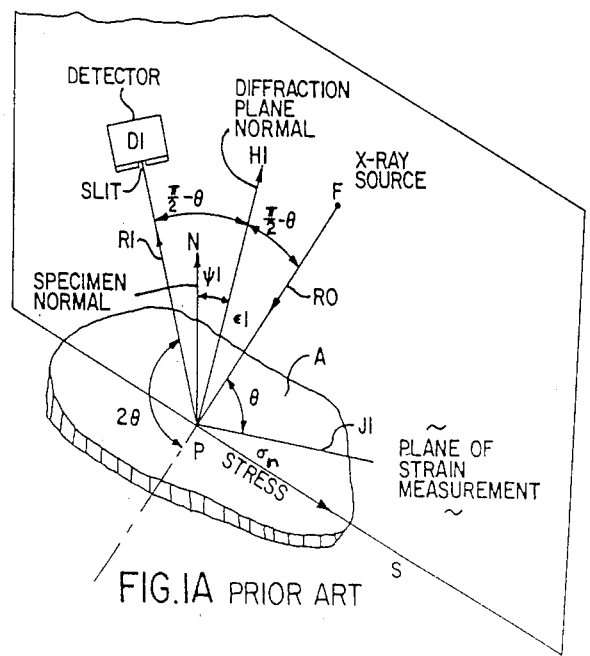
Figure 1B:
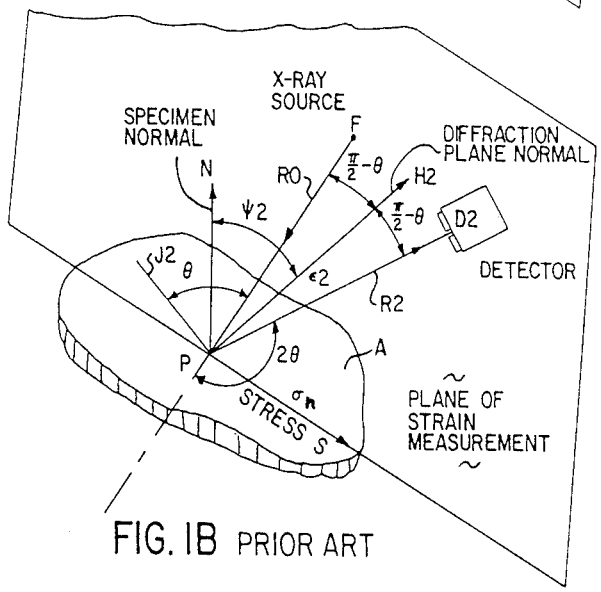

The basic situation is illustrated in FIGS. 1A and 1B where P is the point of measurement on the specimen surface A and PS is the chosen direction. The directions of strain measurement are PH1 and PH2 which are inclined to the surface normal PN at angles $\psi 1$ and $\psi 2$. The normal stress component $\sigma_n$ in the specimen surface is obtained from the difference between lattice strains $\epsilon 1$ and $\epsilon 2$ multiplied by Young's Modulus E and a factor depending on the relative inclinations of the directions PH1 and PH2.

$$\sigma_n = E \cdot (\epsilon 1 - \epsilon 2)/(K1 - K2) \qquad (1)$$

where K1 and K2 are functions of angles $\psi 1$ and $\psi 2$ and Poisson's ratio $\nu$, a known constant of the material, and $$K1 = \sin^2 \psi 1 - \nu \cos^2 \psi 1$$

$$K2 = \sin^2 \psi 2 - \nu \cos^2 \psi 2$$

Figure 3A:
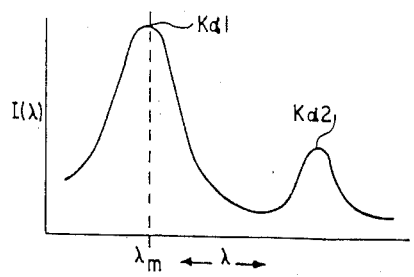
FIGS. 3A to 3D are intensity diagrams plotted against wavelength and diffraction angles.

An X-ray diffractometer for measurement of the spacing of lattice planes in a polycrystalline material consists essentially of an X-ray source F which directs a fine beam R0 of comparatively monochromatic X-rays of known wavelength distribution $\lambda$ (FIG. 3A) at a selected region of the specimen, and a detector D1 or D2 aligned to receive the beam diffracted by a particular set of crystal planes. The wavelength distribution of FIG. 3A is seen to consist of two peaks $K\alpha 1$ and $K\alpha 2$. Other wavelength lines exist which could be used for diffraction.

The detector D1 or D2 is mounted on an arm rotatable about the center P of the irradiated specimen area to measure the diffraction angle $2\theta$ which is determined by the wavelength $\lambda$ and the spacing d (not shown) of the lattice planes, according to Bragg's law of diffraction $$\lambda = 2 d \sin \theta \qquad (2)$$

Here $\theta$ is the angle between the incident beam and the diffraction plane, i.e. between the direction PF and a direction PJ1 or PJ2 normal to PH1 or PH2. For an aligned single crystal specimen a single diffracted ray is emitted, but in a polycrystalline specimen the diffracted rays lie on a cone, each ray originating in a different crystal grain. The diffraction cone intersects the plane of measurement in two directions R1 and R2 shown in FIG. 1A and 1B respectively.

Strain in the direction normal to the lattice planes will cause a change of the interplanar spacing d and, from Bragg's equation, a consequent change in diffraction angle $\theta$. The direction PH1 or PH2, each of which is normal to a diffracting plane, is the bisector of the back reflection angle between the incident and diffracted rays R0 and R1 and lies in the direction of lattice strain measurement at an angle $\pi/2 - \theta$ to the incident beam. The diffraction cone intersects the plane along direction PD1 (diffracted ray R1) and the detector D1 is rotated about the axis through P to determine the diffraction angle $2\theta$.

The lattice spacing can be determined from Bragg's relation (equation 2) from the value $2\theta m$ (FIG. 3B) at the center of the main peak $K\alpha 1$ of the diffraction line, on the assumption that this coincides with the known value $\lambda m$ (FIG. 3A) of the peak of the wavelength distribution. For a deformation free specimen with completely random orientation of small grains the recorded intensity $Tr(2\theta)$ is proportional to the incident beam intensity $I(\lambda)$ and the volume $\Delta V$ of the diffracting grains, i.e.

$$Tr(2\theta) \alpha I(\lambda) \Delta V \qquad (3)$$

The strain in a second specimen direction can be measured by reorienting the diffractometer to bring the diffracting plane normal PH2 into coincidence with the direction of the strain $\epsilon 2$.

The resulting difference $\Delta 2\theta$ in the diffraction angles for the two strain directions gives the lattice strain difference $$\epsilon 1 - \epsilon 2 = (\theta 2 - \theta 1) \cot \overline{\theta} \qquad (4)$$

where $$\bar{\theta} = \frac{\theta 1 + \theta 2}{2} \quad (4)$$

Because this difference in the diffraction angles for the two strain directions is used to determine the stress from equation 1, it is unnecessary to determine ε1 and ε2 individually, thus avoiding a need for a strain free sample of the particular specimen material.

Instead of reorienting the diffractometer or the specimen between strain measurements, an alternative procedure can be used in which the instrument and specimen remain fixed for the two strain determinations. Due to the intersection of the diffraction cone with the plane of strain measurement, a second diffracted beam R2 in direction PD2 lies on the opposite side of the incident beam, as shown in FIG. 1B. The diffraction plane normal lies along PH2 at an angle λ/2−θ to the incident beam R0 and at twice that angle to the direction PH1. If a second detector D2 is suitably located, lattice strain measurements can be made simultaneously in directions PH1 and PH2.

The method in which the diffractometer has to be reoriented between two separate lattice strain measurements is known as the double exposure technique (DET) while the simultaneous observation with two detectors is known as the single exposure technique (SET).

Figure 3B:
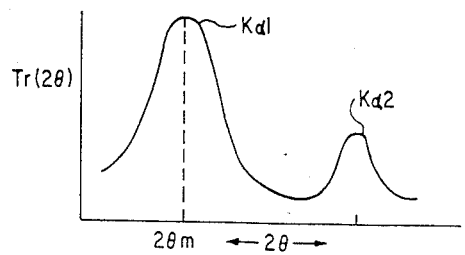
Figure 3C:
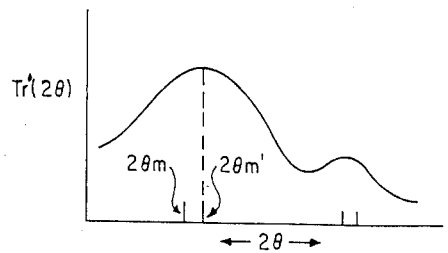

In principle a strictly monochromatic X-ray beam and a deformation free specimen under stress would produce a sharp diffraction line having a width of less than 1 minute of arc, from which the strain could be measured precisely. In practice the characteristic wavelength distribution (FIG. 3A) will produce a similar diffracted intensity distribution on a scale of 2θ for a deformation free specimen of completely random orientation of small grains, as shown in FIG. 3B. Broadening and distortion of the line can occur from instrumental factors, principally the source width, and further broadening will occur in specimens deformed by cold work or specimens having a grain size below 0.1 micron, both of which effects can produce line widths of several degrees (FIG. 3C). Line broadening will cause a shift in the peak of the diffraction line away from the 2θm value corresponding to the wavelength maximum, to the intensity maximum at 2θm', due to overlapping of the Kα1 and Kα2 components. This will produce an error in lattice parameter measurement. Where the line profiles are the same for both directions in which lattice strain is measured, the angular shift due to broadening will be the same, and, from equation 4, the strain difference will be unchanged. Errors due to unequal line distortion can be corrected by profile analysis procedures based on a full diffraction line intensity distribution, rather than peak intensity or line center measurement.

In the counter type of diffractometer the diffraction line intensity is measured by step scanning in increments of 2θ, by rotating the detector. If the specimen remains fixed during the scan a progressive change in the diffraction direction in the specimen will take place. This effect is shown in FIG. 2A. A scan through ω from 2θ to 2θ' will change the direction of strain measurement from PH1 to PH1' on the bisector of the new back reflection diffraction angle λ−2θ'. The new lattice strain direction PH1' will have a direction at an angle ψ' to the specimen normal PN. The change from ψ to ψ' will be equal to the change in the angle Δθ of the diffracting plane to the incident beam direction.

$$\psi' = \psi + \omega/2 \quad (5A)$$

where $$2\theta' = 2\theta + \omega \quad (5B)$$

The counter type of diffractometer has now been replaced for many applications by the position sensitive detector diffractometer which employs the recently developed position sensitive X-ray detectors to replace photographic and other methods of detecting X-rays.

The nature and performance of position-sensitive detectors are known, for example, from Borkowski et al. U.S. Pat. Nos. 3,483,377 of Dec. 9, 1969, Ruud, 4,042,825 issued Aug. 16, 1977 and Sparks et al 4,076,981 issued Feb. 28, 1978. Such detectors collect the full X-ray diffraction line simultaneously and increase the speed of operation by a factor of at least fifty times compared with some earlier diffractometers.

A situation similar to that described above in the counter type of diffractometer exists in a diffractometer using a position sensitive detector. A schematic drawing is shown in FIG. 2B. The position sensitive detector D1 is set with its center at Xo which corresponds to where the aperture in the counter type detector was positioned, with the sensitive area normal to the axis PXo. The output of the detector is fed to a computer where it is separated into a number (say 500) of channels i.e. typically 0.01° per channel. The position X' of each diffracted X-ray is sensed by the instrument and the number of photons received within each channel of width ΔX is summed during a fixed time interval. The X-ray diffraction pattern over the sensitive length of the detector is recorded simultaneously to build a complete diffraction line. The intensity values over the diffraction line are expressed by the computer in the form of a histogram, i.e. a series of numerical values each corresponding to the number of pulses received by a given channel. In a typical example, a smaller group, (say 250) of these channels, is selected to cover the extent of the diffraction line.

The intensity recorded at the position X' at an angle α to the reference position Xo is due to diffraction at an angle 2θ'. The tilt angle ψ' of the new lattice strain direction PH1' to the normal PN will be displaced by α/2 from the direction PH1, and $$\psi' = \psi + \alpha/2 \quad (6A)$$

where $$2\theta' = 2\theta + \alpha \quad (6B)$$

In both the counter and position sensitive detector instruments the strain direction PH1' in the specimen changes with diffraction angle 2θ'. If the volume ΔV of the diffracting grains varies irregularly with specimen direction PH1', the measured intensity Tm(2θ) (FIG. 3D) will be different from the intensity Tr'(2θ) (FIG. 3C) for a specimen having a completely random orientation of small grains, and if w(H) is the ratio of these diffracting volumes $$Tm(2\theta) = w(H) \cdot Tr'(2\theta) \quad (7)$$

Figure 3D:
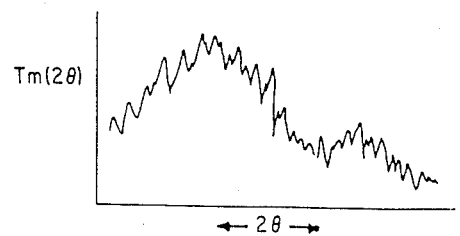

The effect of irregular grain distribution on the diffraction line is shown in FIG. 3D. This effect can be avoided in the counter diffractometer if the specimen direction PH1 is held constant by mechanical rotation of the specimen through one half the scan angle $\omega$ (equation 5A). This is a feature of laboratory stress diffractometers, used with small portable specimens which can be mounted on the instrument.

In the position sensitive detector diffractometer, the continuous change in strain direction, with the resultant changes in grain orientation, also produce variations in the diffraction line intensity distribution, as shown in FIG. 3D.

Variations due to irregular grain distribution occur most frequently in measurement of stress gradients where the beam width is narrow, reducing the number of diffracting grains, and in specimens having a large grain size.

An additional factor which can introduce error in strain measurement is defocusing of the diffraction line due to incident beam divergence, especially when the length of the irradiated area of the specimen in the stress direction is large. Where the diffracting power of the specimen varies over this length, defocusing will produce an asymmetric distribution which, because it acts at each point over the diffraction line, will cause a displacement of the resultant line, and a corresponding error in strain measurement.

Diffractometer misalignment is another factor leading to error in stress measurement. The principal alignment error is that due to displacement of the rotation center of the instrument from the point P on the specimen surface. This produces a displacement of the diffraction line of a similar magnitude. In the single exposure technique this error is compensated by equal displacements in $2\theta$ of the two diffraction lines. This is not the case in the double exposure method where a residual error occurs, dependent on the tilt values used.

In summary, a well designed stress diffractometer should produce a smooth diffraction line having the intensity distribution of a completely random specimen even in cases where the grain size is large or where a small diffracting volume must be used; focusing of the detectors must be provided; and the alignment error should be controlled. Analysis of the line position should be based on the full intensity distribution of the diffraction line.

The scanning diffractometer, using a proportional counter, or a scintillation counter to measure diffracted intensity at a series of diffraction angles in order to produce a diffraction line intensity distribution, has been the standard laboratory instrument for powder diffraction for many years. The instrument has been adapted for stress measurement by using specimens tilted to vary the lattice strain direction, and which are rotated by the scanning mechanism. Fixed specimens can be examined by the equi-inclination method in which both tube and detector are scanned through equal angles but in opposite senses, to keep the diffraction direction constant in the specimen.

Indeed, most of the forms of apparatus developed in the past have been essentially laboratory instruments, that is to say they are not portable and perform best under controlled laboratory conditions. As such, these instruments are unsuitable for work in the field, e.g. for the inspection of large structures, such as bridges, pipelines etc. To determine stresses in structures in the field, there is a need for a reliable and accurate portable diffractometer, and some workers in the art have already begun to develop such devices. Examples of such development will be referred to more fully below.

Portable instruments for fixed specimens have been designed which do not use equi-inclined geometry, and consequently are subject to irregularity in intensity distribution due to variation in the orientation factor with specimen direction.

Specific Prior Art Instruments

Various patents have issued in this field, for example:

| Bertram | U.S. Pat. No. 2,184,174 | December 19, 1939 |
| --- | --- | --- |
| Firth | U.S. Pat. No. 2,462,374 | February 22, 1949 |
| Khol | U.S. Pat. No. 2,898,470 | August 4, 1959 |
| Khol | U.S. Pat. No. 3,030,507 | April 17, 1962 |
| Weinman | U.S. Pat. No. 3,402,291 | September 17, 1968 |
| Sekita | U.S. Pat. No. 3,634,686 | January 11, 1972 |
| Shimura | U.S. Pat. No. 3,639,758 | February 1, 1972 |
| Mizunuma | U.S. Pat. No. 3,639,760 | February 1, 1972 |
| Ogiso | U.S. Pat. No. 3,868,506 | February 25, 1975 |
| Bens | U.S. Pat. No. 3,934,138 | January 20, 1976 |
| Cohen et al | U.S. Pat. No. 4,095,103 | June 13, 1978 |
| Erwin | U.S. Pat. No. 4,125,771 | November 14, 1978 |
| Nagao et al | U.S. Pat. No. 4,128,762 | December 5, 1978 |
| Kramer et al | U.S. Pat. No. 4,287,416 | September 1, 1981 |

One instrument that provides for constant specimen strain direction during measurement is that of Sekita. The instrument uses a fixed X-ray tube and a scanning detector driven along a circular arc centered on the specimen in order to scan the diffraction line. As shown in Sekita's FIG. 7 the diffractometer is mounted on an arm connected to an axle, the axis of which passes through the detector rotation axis at the specimen surface. This enables the whole diffractometer to be rotated to give a desired direction of lattice strain measurement in the specimen. Sekita uses a combined scan, in which the detector rotates through an angle $\omega$ relative to the X-ray source and the arm counter rotates the source and the detector together through $-\omega/2$. This gives equal and opposite relative rotations of source and detector, providing equi-inclination geometry. The two rates of rotations must be coordinated.

In the form shown, the axle extends below the surface plane of the specimen, so that the instrument can only be used with fixed specimens in limited situations that permit the arm rotation axis to meet the specimen surface.

Of the other prior patents listed above, of particular interest are the instrument using a proportional counter position sensitive detector disclosed by Cohen et al., and the two detector instrument shown by Bens. These are portable instruments which have the detector, or detectors, fixed relative to the X-ray source.

The Bens instrument uses two proportional counter position sensitive detectors mounted integrally with the X-ray source, as shown in his FIG. 3. The assembly is arranged so that the beam from the X-ray source is incident on a specimen at 0, the detectors being aligned with their X-ray sensitive surfaces tangent to the respective diffracted X-ray beams. The assembly is mounted pivotally about an axis through 0 normal to the diffraction plane so that the angle $\psi$ between the specimen diffraction direction and the specimen surface normal N can be set to a desired value. The two diffraction patterns are recorded simultaneously by the single exposure method.

In this instrument the source and the detectors are rigidly assembled together and there is no possibility of rotating the X-ray tube about the axis O relative to the detectors.

The Cohen et al instrument uses a single proportional counter position sensitive detector mounted integrally with the X-ray tube, as shown in their FIG. 3. The detector 11 is aligned with the center of its sensitive surface normal to the diffracted X-ray beam. The tube 10 and detector 11 form an assembly that is mounted to move in an arc centered on the specimen surface, so that the angle of the measured specimen strain direction to the specimen normal can be changed. Stress is measured by two or more determinations of lattice strain, i.e. using the double exposure method. The rigid tube and detector mounting precludes rotation of the X-ray tube relative to the detector.

In both these instruments, the observed diffraction lines will be subject to intensity fluctuations from irregularities in the grain orientation factor over the diffraction line, as explained above in relation to equation 7.

No provision for change of focus with specimen tilt has been made in the Cohen et al instrument. In the Bens instrument, as shown in FIG. 3, the detector radii are equal to each other while being less than the source radius in order to minimise the defocusing effect. In a specimen of irregular grain orientation, defocusing has been shown to produce a virtual strain displacement, which will be present in both these instruments.

Herbert E. Göbel in a paper entitled "A new method for fast XRPD using a position sensitive detector." published in Advances in X-ray Analysis, Volume 22, pages 255-265, 1979, has proposed an instrument that employs scanning with a position sensitive detector in a standard diffractometer having a rotatable specimen to obtain high speed powder diffraction patterns. The diffraction line at each scan step is collected by microcomputer. Step scanning with this arrangement enables the intensities at each step to be summed according to diffraction angle. Specimen rotation keeps the range of strain directions constant with detector position, and the resultant line has a constant range of grain orientations for all diffraction angles, giving a smooth resultant diffraction line with intensity proportional to $Tr'(2\theta)$ in equation 7 above.

SUMMARY OF THE INVENTION

The present invention relates to apparatus and methods in which an X-ray beam is projected onto the surface area of a polycrystalline specimen in which stress is to be measured, and X-rays diffracted by a set of crystal lattice planes in said area are received in a position sensitive detector, or preferably in two such detectors for operation in the single exposure mode. The X-rays received in each detector are ultimately converted into a diffraction array of intensity values as a function of diffraction angle. In the specific example given below, this conversion is carried out in two steps. Firstly, in the detector the received X-rays are converted into a preliminary array of intensity values as a function of channel position. This preliminary array is then transformed in the computer into the diffraction array in which the intensity values are stored as a function of diffraction angle. The projected beam is step scanned angularly about the specimen area to generate a sequence of such diffraction arrays. The intensity values of said diffraction arrays are then averaged for each of a series of diffraction angles ($2\theta$). The resulting average values constitute a histogram from which a computer can calculate the $2\theta$ value of a preselected characteristic in the diffraction line, such as the K$\alpha$1 peak. The two values so obtained (either from separate detectors used simultaneously or from one detector used in the double exposure technique) can be used to determine a strain difference, from which the stress can be calculated.

The characterising feature of the present invention resides in the fact that the intensity values so averaged are restricted to those that measure strain in a selected range of directions about a chosen mean strain direction in the specimen by restricting the intensity values averaged to those lying within a virtual window in the detector that is such that the centre of width of the window is coincident with the diffracted beam received from lattice planes in the specimen normal to the chosen mean strain direction and the angular width of the window is equal to twice the selected range. To achieve this effect the window is displaced relative to the diffraction array for each successive scanning position. The effect is to obtain a resultant diffraction line intensity distribution that is substantially equivalent to that of a specimen having a completely random orientation of small grains.

An important feature of the invention is that it permits operation with a fixed specimen and hence adaption as a portable instrument for use in the field with large specimens. It achieves the advantages of an instrument having equi-inclination geometry without the severe practical complications of the need to scan the source and detector accurately by equal amounts in opposite directions (or to rotate the specimen). This effect is achieved by the window displacement which amounts to a virtual scanning of the detector.

Figure 4A:
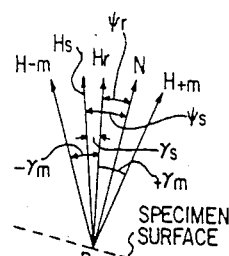
FIGS. 4A and 4B are diagrams corresponding to FIGS. 1A–2B but illustrating the special conditions of the present invention.
Figure 4B:
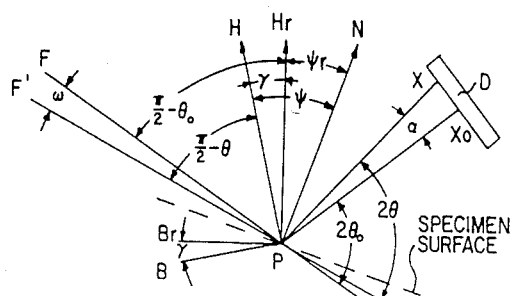

The effect of using a fixed specimen and scanning the source is illustrated in FIGS. 4A and 4B. The said chosen mean strain direction Hr lies at an angle $\psi r$ to the specimen normal PN. In the measurement of lattice strain in the present method, the selected range of lattice strains about the mean strain direction is chosen to extend from H+m to H−m (FIG. 4A) equidistant about the mean strain direction Hr at angles $+\gamma m$ and $-\gamma m$. The angle $\gamma s$ between Hr and a direction Hs at an angle $\psi s$ to the specimen normal PN is $$\gamma s = \psi s - \psi r \tag{8A}$$

and for Hs within the range of lattice strain directions $$|\gamma s| \leq |\gamma m| \tag{8B}$$

The diffraction line values derived in the analytical procedure described below are limited to contributions from this range of directions, known as the "region of interest" and defined by the virtual window, the width of this window therefore being $4\gamma m$.

Figure 5A:
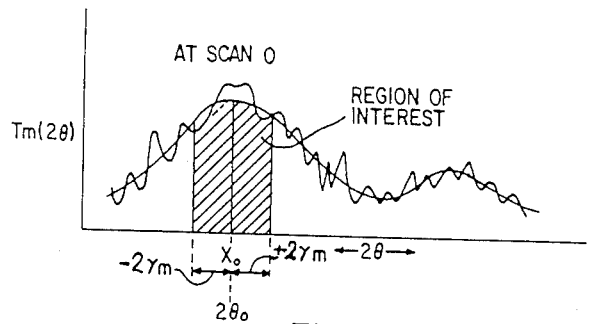
FIGS. 5A and 5B are intensity diagrams also illustrating the present invention.

At the scan start, referred to as scan O and shown in FIG. 5A, the X-ray beam from source F is diffracted from planes parallel to the plane PBr having normals along Hr at $\psi r$ to the specimen normal PN and is received by the detector D at Xo having been diffracted through the angle $2\theta o$ (FIG. 4B).

Following a scan of the source through an angle $\omega$ to F', diffraction by planes parallel to the plane PB having the diffraction normal H at an angle $\gamma$ to Hr are received in the detector at X at an angle $\alpha$ to Xo.

For the detector position X the diffraction angle $2\theta$ is given by the equation $$2\theta = 2\theta_0 - \omega + \alpha \tag{9A}$$

The diffraction direction H at an angle $\gamma$ to Hr gives the equation $$2\theta = 2\theta_0 - 2\omega + 2\gamma \tag{9B}$$

From these equations the displacement $\gamma$ can be expressed as $$\gamma = (\omega + \alpha)/2 \tag{9C}$$

Figure 5B:
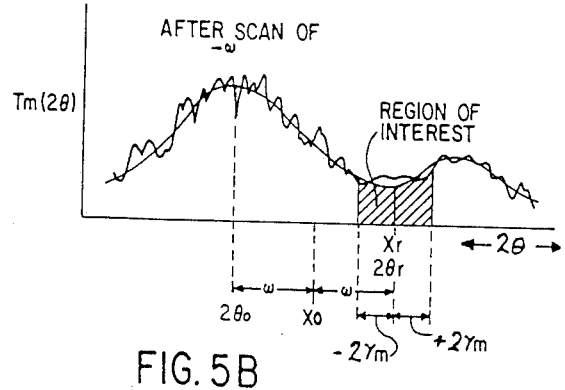

A scan through an angle $-\omega$ produces the situation shown in FIG. 5B. The defined specimen direction Hr for which $\gamma = 0$ will have the detector position Xr at an angle $+\omega$ to Xo, where $$2\theta r = 2\theta_0 + 2\omega \tag{9D}$$

The region of interest extends in the detector from $X - m$ to $X + m$, which correspond to the angles $-2\gamma m$ and $+2\gamma m$.

In step scanning, the scan step $\Delta\omega$ can be chosen as a multiple of the angular channel width $\Delta\alpha$ in order to give $2\theta$ displacements of an integral number of channels. When the value of $2\theta$ is held constant, a scan through each step of $\Delta\omega$ moves the detector position of $2\theta$ from X to X' through the angle $\Delta\omega$. At the same time the centre of the region of interest in the detector moves from Xr to Xr' through an angle $-\Delta\omega$ so that the relative motion of a given $2\theta$ value across the region of interest is $2\Delta\omega$.

For a given $2\theta$ value, the intensities are included when the diffraction direction H lies within the region of interest and the average intensity over this region, $Ts(2\theta)$ is calculated. This will be related to the value $Tr'(2\theta)$ for a specimen with completely random orientation of small grains, as given in equation 7. For n values that fall within the window the average intensity $Ts(2\theta)$ is $$Ts(2\theta) = W \cdot Tr'(2\theta) \tag{10A}$$

where $$W = \frac{1}{n} \sum_{H-m}^{H+m} w(Hs) \tag{10B}$$

and where Hs is the direction of H for the $2\theta$ value under consideration.

For a sequence of $2\theta$ values taken at equal intervals $2\Delta\omega$, the same set of specimen directions will be involved at each value of $2\theta$, and W will be a constant over the diffraction line. When the step $\Delta\omega$ is greater than the channel width $\Delta\alpha$, then $2\theta$ values within a single step will be generated by different sets of specimen directions, rotated by increments $\Delta\gamma = \Delta\alpha/2$ and each belongs to a separate $2\theta$ sequence having intervals $2\Delta\omega$. Where $\Delta\omega$ is small the rotation can be expected to leave the W summation substantially unchanged.

DETAILED DESCRIPTION OF THE PREFERRED EMBODIMENT

Figure 6:
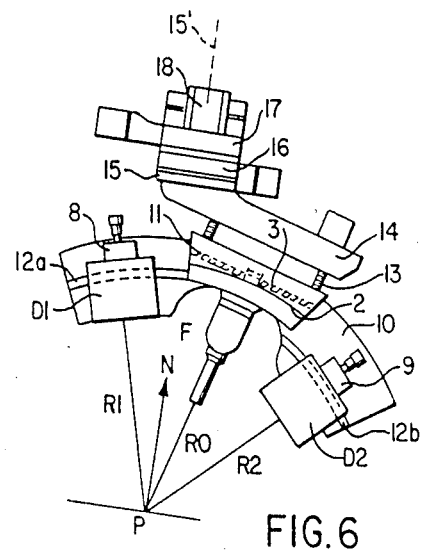
FIG. 6 is a schematic view of an embodiment of apparatus according to the invention.

An embodiment of the invention is shown schematically in FIG. 6. A miniature X-ray tube F is mounted on a curved slide 2 and is driven in an arc about the center P. The tube is driven by a conventional screw and split nut arrangement 3 connected to a Slosyn stepping motor through bevel gears (not shown). The X-ray tube mount and drive assembly 11 is fixed to a frame 10. Two proportional counter position sensitive detectors D1 and D2 are mounted on micrometer driven slides 8 and 9 at either end of the frame 10 for adjustment along the radial direction. For adjustment in the circumferential direction, the detectors are mounted on arcuate tracks 12a and 12b centered at P, so that the interdetector angle, i.e. between radii R1 and R2, can be set to the required value for the single exposure method, i.e. $2\pi - 4\theta m$.

Figure 7:
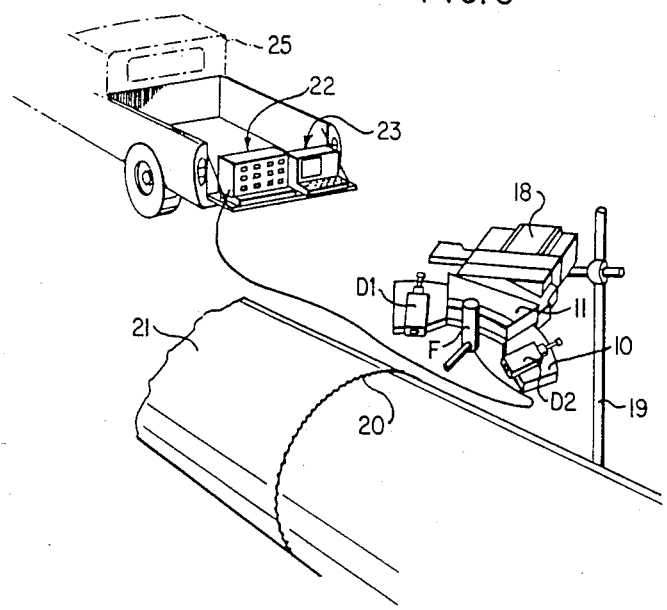
FIG. 7 is a pictorial representation of a way in which such apparatus can be used.

The assembly 11 carries four screw threaded posts 13 that enter a drive mechanism 14, whereby the instrument can be translated along the axis PF of the X-ray tube in order to set the rotation axis P on the specimen surface. The mechanism 14 is in turn attached to the rotatable disc 15 of a rotation mount 16 so that the instrument can be rotated about the normal to the specimen surface to align the plane of the instrument in the direction in which stress is to be measured. The axis 15' of the rotation mount is set coincident with the normal PN to the specimen surface. Two translation drives 17 and 18 carry the rotation mount 16, so that the instrument can be traversed in X and Y directions parallel to the specimen surface. The drive 18 is attached to a suitable mount, for example a support structure 19 as shown in FIG. 7. This figure also shows how the X-ray tube F can be directed at a section of a weld 20 in a pipeline 21. A detector analysis system 22, a computer 23 and a power source (not shown) can conveniently be mounted on a nearby vehicle 25. The computer will preferably include disc storage and a printer for furnishing a permanent data record of all aspects of the stress measurement. A video terminal is part of the computer for control and output of stress measurements in real time together with graphs of the resultant diffraction lines.

In operation in the single exposure mode the detectors D1 and D2 are set to measure lattice strain in the specimen in two directions inclined to each other at an angle of $\pi - 2\theta m$, the first of these directions usually being chosen along the specimen surface normal. Each detector radius Rd1 and Rd2 is set to the required focal distance which, for a source radius Rf, is determined from the equation $$Rd1 = Rf \sin(\theta m - \psi 1)/\sin(\theta m + \psi 1) \tag{11A}$$

$$Rd2 = Rf \sin(\theta m - \psi 2)/\sin(\theta m + \psi 2) \tag{11B}$$

As above indicated, the scanning takes the form of stepwise rotational movement of the X-ray source F about the irradiated area on the specimen, the size of each such scanning step being $\Delta\omega = n\Delta\alpha$. Since the diffracted beam from an individual grain in the specimen thus advances by 2n channels for each scanning step, each grain passes through a series of scanning steps encompassing the range of $2\theta$ values.

Figure 8:
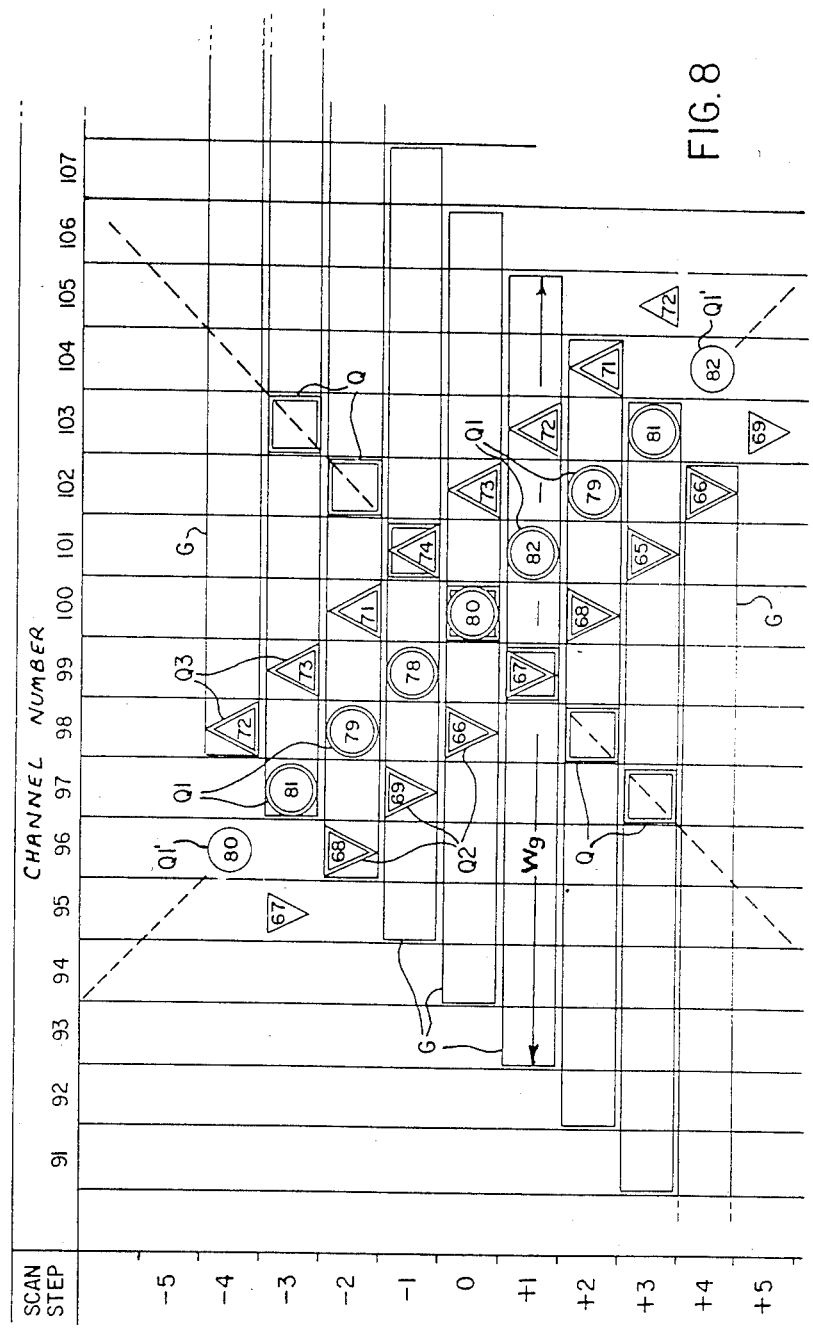
FIG. 8 is a diagram illustrating the analysis procedure used in the present invention.
Figure 9:
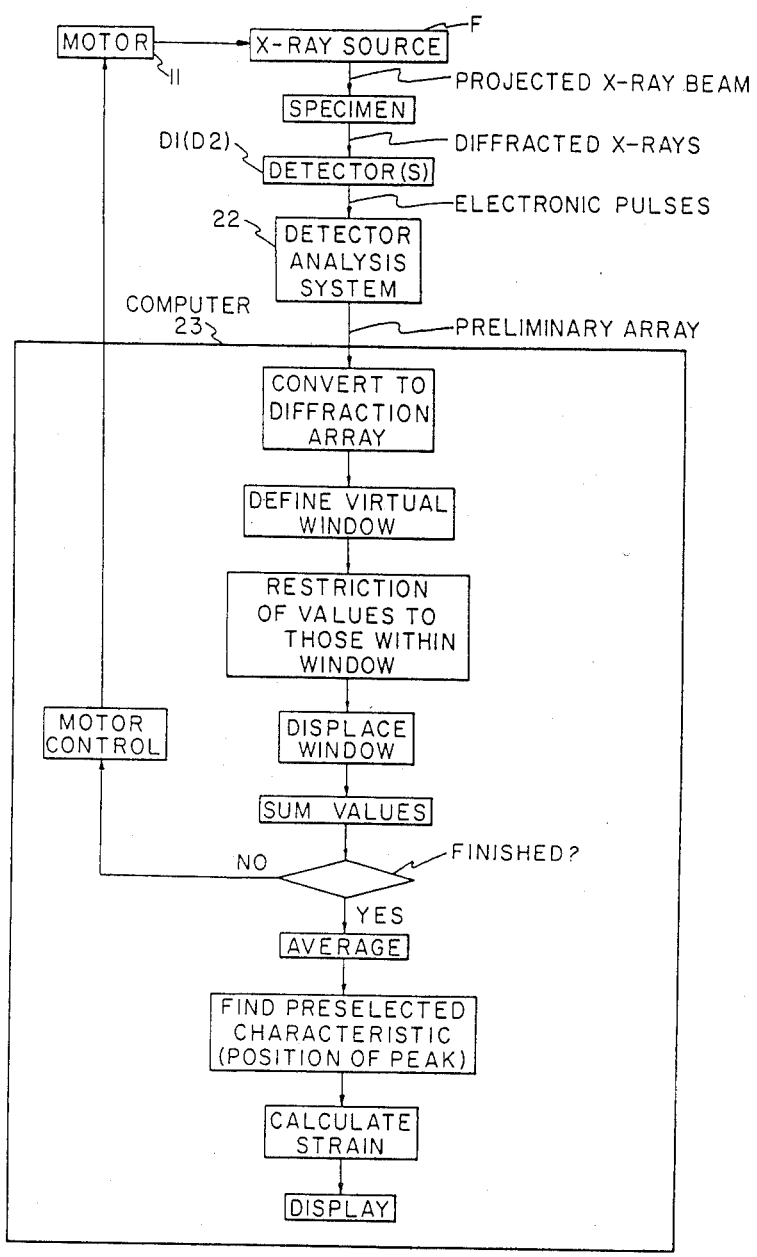
FIG. 9 is a flowchart.

The averaging procedure is carried out in the computer in a manner that is illustrated pictorially in FIG. 8 and as a flowchart in FIG. 9. This figure necessarily shows only some of the detector channels involved (arbitrarily chosen as those designated 91-107). In practice, each detector may have about 500 channels. Of these about 250 will cover the entire diffraction line, and the X-ray source F will be arranged to scan about the same number of steps e.g. 250. However, the region of interest shown in FIGS. 5A and 5B, which can conveniently be referred to in the analytical procedure as a virtual window, will be a substantially smaller group, e.g. 100 channels wide. This virtual window is shown in FIG. 8 by the rectangle G, which for convenience of illustration is here shown having a width Wg of only 13 channels. At scan O the window begins at channel 94 and ends at channel 106, being centred on channel 100. Within this window G, there are shown some arbitrary individual intensity values recorded for each channel in the detector, which values will have been transferred to the computer memory for each scan position. At each scanning step the window G is moved n channels (assumed in FIG. 8 to be one channel) in one direction, e.g. to the left when the scan is positive, so that at scan +1 it extends from channel 93 to 105, no longer including channel 106.

At a given scan position, each channel corresponds to a given $2\theta$ value, and, with each scan step, this $2\theta$ value moves to an adjacent channel, e.g. to a higher channel number for positive scan steps and to a lower channel number for negative scan steps. This movement is in the opposite direction to that of the window G. Hence, for each scan step, a given $2\theta$ value moves along the window G, moving at a relative rate of two channels per step in this example. The intensity values recorded for a given $2\theta$ value in successive scan steps are summed only if they fall within the window G. This sum is then divided by the number of values summed to give an average intensity value for the given $2\theta$ value.

To illustrate this point, one set of $2\theta$ values Q1 that is so averaged is shown with each intensity value surrounded by a double circle. There are 7 such intensity values Q1, and the average so obtained corresponds to position $2\theta o$. It will be noted that the values Q1' shown in single circles are not included, since, although they have the same $2\theta$ value and thus lie on the diagonal line extending through the values Q1, they are beyond the ends of the window G.

Simultaneously the computer will determine the average of the intensity values Q2 (shown in double inverted triangles) of which there are also 7 to generate another average value that corresponds to $2\theta o + 2\Delta\alpha$.

Similarly the erect triangles Q3 signify another set of seven intensity values for $2\theta o - 2\Delta\alpha$. The summation for the intermediate values of $2\theta o + \Delta\alpha$ and $2\theta o - \Delta\alpha$ are not shown but exist and will be similarly averaged. In this case there are only six such intensity values for each $2\theta$ value within the window G.

The preliminary array referred to above is hence a sequence of intensity values shown against channel position (channel number) for a given scan position, i.e. a horizontal row in FIG. 8. With each step the window G moves by a first increment (one channel in the example) relative to a reference channel, e.g. the channel 100.

The corresponding diffraction array is the same sequence of intensity values also extending as a horizontal row in FIG. 8, but as a function of diffraction angle. With each scan step, the reference diffraction angle value, e.g. that represented by the values Q1, and lying along a diagonal in FIG. 8 from top left to bottom right, moves relative to the reference channel in the opposite direction from that of the window, so that the window has a displacement relative to the reference diffraction angle value by a second increment which in the example is twice the first increment.

It will be apparent that, measured from the centre Q (shown by squares) of the window G, each successive movement of the intensity value for a given $2\theta$ corresponds to two channels.

For each scan the computer examines the intensity value for each channel in each detector and computes the diffraction angle $2\theta$ from equation 9A and the displacement $\gamma$ from equation 9C.

From this $\gamma$ value the computer determines from equation 8B whether the intensity value is within the window G. If it is not, the value is disregarded. Those intensity values that are found to lie within the window G are then averaged for each $2\theta$ value.

The computer will generate such average values separately for each detector.

For each detector these results constitute a resultant histogram of average intensity values plotted against $2\theta$ values from which the computer can calculate the $2\theta$ value of the $K\alpha 1$ peak or any other preselected characteristic of this resultant histogram in accordance with known analytical procedures. See the paper entitled "Location of Diffractometer Profiles in X-ray Stress Analysis," D. Kirk et al, published at page 283 of "Advances in X-ray Analysis" Vol. 20, Plenum Press, 1977.

From these characteristic values ($\theta 1c$ and $\theta 2c$), the strain difference $\epsilon 1 - \epsilon 2$ can be obtained from equation 4 by solving the expression $$\epsilon 1 - \epsilon 2 = (\theta 2c - \theta 1c)\cot\left(\frac{\theta 1c + \theta 2c}{2}\right) \qquad (12)$$

Once the value of $\epsilon 1 - \epsilon 2$ is known, the value of the surface stress component $\sigma_n$ (the desired result) follows from equation 1.

The choice of parameters for the scan affects the accuracy and speed of stress measurement.

The width of the region scanned in the position sensitive detector, called the scan width Ws, is preferably chosen as the sum of the diffraction line width and the maximum expected strain displacement. The diffraction line width is a function of the wavelength distribution, the instrumental broadening distribution and the lattice deformation distribution. Where these are assumed to be approximately Gaussian, the resultant diffraction line width Wr can be determined from the relation $$Wr = (Wa^2 + Wi^2 + Wd^2)^{\frac{1}{2}} \qquad (13)$$

where

Wa is the width at half maximum intensity of the wavelength distribution,

Wi is the width of the instrumental broadening distribution, and

Wd is the width of the lattice deformation distribution.

In the case of the $K\alpha$ doublet, the two component distributions $W\alpha 1$ and $W\alpha 2$ will be separated by the peak displacement W12 of the components.

The total scan width Ws for the doublet is then $$Ws = Wr + W12 + Wx \qquad (14)$$

where Wx is the maximum strain displacement.

Where the $K\alpha$ doublet is resolved and only a single component $K\alpha 1$ is used, $Ws = Wr + Wx$ Where another characteristic is chosen, such as the line centroid, the scan width Ws must include the full $K\alpha$ doublet.

The window width Wg determines both the degree of resolution of the lattice strain in the chosen direction in the specimen and the speed of the data collection. The angular spread $2\gamma m$ of the diffraction directions in the specimen which contribute to the resultant diffraction line, is one half the angular window width. The limiting effective value of the window width occurs when it approaches the resolution limit between adjacent strain directions. This window width Wg is equal to the diffraction distribution Wm for strictly monochromatic radiation, which is the resultant of the instrumental broadening and lattice deformation distributions $$Wm = (Wi^2 + Wd^2)^{\frac{1}{2}} \quad (15)$$

The smaller the width Wg, the higher the precision of the strain measurements and the resultant stress determination. However, if the width Wg is made too small, the speed of operation suffers.

The speed of data acquisition is thus controlled by the window width Wg. At a given $2\theta$ value the speed factor Sf, i.e. the ratio of the intensity of the resultant line obtained in scanning to the total intensity is $$Sf = Wg/(Wg + Ws) \quad (16)$$

When the window width Wg is equal to the scan width Ws, the factor Sf is 0.5 and this can be considered to be the maximum window width, since further increase in window width results in decreased resolution for an inadequately compensating speed increase.

The magnitude of the scan step $\Delta\omega$ is limited by the width of the diffraction distribution for strictly monochromatic radiation, since sequential scan steps will give adjacent distributions for a given set of diffracting grains of the same alignment which are at the limit of resolution. Intensity fluctuations in the resultant diffraction line for this grain set would occur. A fraction f1 of this width (for example, f1 could equal $\frac{1}{3}$ or $\frac{1}{4}$) can be used to insure a smooth diffraction line.

In the use of the virtual window, a uniform weighting of the intensity distribution across the window has been assumed. It is possible that an advantage could be obtained by weighting the measured intensities by their positions in the window, for example, giving a higher weight to diffraction directions close to the specimen mean strain direction.

Typical values for the resultant diffraction line width and the $K\alpha$ doublet width are shown in Table 1.

TABLE 1

| | | | Diffraction Line Components Strain $\times 10^6$ | | | | |
|---|---|---|---|---|---|---|---|
| | 1 Specimen Lattice Deformation Distribution Wd | 2 Instrumental Broadening Distribution Wi | 3 Resultant of columns 1 & 2 (equation 15) Wm | 4 $K\alpha 1$ width Wa | 5 $K\alpha 1$ resultant (equation 13) Wr | 6 $K\alpha$ doublet peak separation W12 | 7 $K\alpha 1, \alpha 2$ doublet (equation 14) Wr + W12 |
| 1 | 0 | 530 | 530 | 500 | 730 | 1700 | 2430 |
| 2 | 500 | 530 | 730 | 500 | 880 | 1700 | 2580 |
| 3 | 1000 | 530 | 1130 | 500 | 1240 | 1700 | 2940 |
| 4 | 2000 | 530 | 2070 | 500 | 2130 | 1700 | 3830 |

The corresponding values of the scan width Ws, window width Wg and scan step $\Delta\omega$ are shown in Table 2A for the resolved $K\alpha 1$ component and in Table 2B for the $K\alpha 1, \alpha 2$ doublet.

TABLE 2A

| | | | Scan Constants $K\alpha 1$ Resolved Peak Measurement Strain $\times 10^6$ | | | |
|---|---|---|---|---|---|---|
| | 1 Width of resolved $K\alpha 1$ resultant Wr + W12 | 2 Expected elastic strain displacement Wx | 3 Preferred scan width Ws | 4 Window Width Wg Minimum** | 5 Window Width Wg Maximum | 6 Scan step $\Delta\omega$ = Wm $\times$ f1*** |
| 1 | 730 | 1000 | 1730 | 530 | 1730 | 140 |
| 2 | 880* | 1000 | 1880 | 730 | 1880 | 180 |

TABLE 2B

| | | | Scan Constants $K\alpha 1, \alpha 2$ Resolved Peak Measurement Strain $\times 10^6$ | | | |
|---|---|---|---|---|---|---|
| | 1 Resultant $K\alpha 1, \alpha 2$ doublet width | 2 Expected elastic strain displacement | 3 Preferred Scan width Ws | 4 Window Width Wg Minimum** | 5 Window Width Wg Maximum | 6 Scan step $\Delta\omega$ = Wm $\times$ f1*** |
| 1 | 2430 | 1000 | 3430 | 530 | 3430 | 140 |
| 2 | 2580 | 1000 | 3580 | 730 | 3580 | 180 |
| 3 | 2940 | 1000 | 3940 | 1130 | 3940 | 280 |
| 4 | 3830 | 1000 | 4830 | 2070 | 4830 | 520 |

*$K\alpha 1$ resolution limit
**Strain resolution limit
***Assuming f1 = $\frac{1}{4}$ The above values which are in units related to strain can be converted to angles $\Delta 2\theta$ corresponding to the angular width in the detector, or to a number of channels Nc (rounded out to an integer), as follows:

$$\Delta 2\theta = 2\epsilon \tan\theta \qquad (17A)$$

$$Nc = \Delta 2\theta \times Cd \qquad (17B)$$

where
$\epsilon$ is the strain value in the above tables
Cd is a constant representing the number of channels per degree, and
$\theta$ is the diffraction angle for the chosen reflection.

For a ferritic iron specimen with chromium K$\alpha$ radiation the value of $\theta$ is approximately 78°. Putting this value into equation 17A, for the minimum and maximum values of Wg, i.e. $\epsilon = 530 \times 10^{-6}$ and $4830 \times 10^{-6}$ gives values for $\Delta 2\theta$ of 0.29° and 2.60°. In equation 17B, where Cd is assumed to be 100, the corresponding values for Nc are 29 and 260.

An austenitic steel specimen with chromium K$\beta$1,3 radiation has an approximate value for $\theta = 74.2°$. The K$\beta$ line width is $882 \times 10^{-6}$. Putting these values in equation 17A for the minimum and maximum values of the window width Wg, $\epsilon = 530 \times 10^{-6}$ and $2462 \times 10^{-6}$ gives values for $\Delta 2\theta$ of 0.22° and 0.997°. The corresponding values of Nc where Cd is assumed to be 100 in equation 17B are 22 and 100 channels. The reduced width of the maximum window value in this example is due to the smaller width of the chromium K$\beta$1,3 doublet compared with the chromium K$\alpha$ doublet.

Alternative Procedure

The present arrangement in which the X-ray source is scanned and two detectors are used permits an alternative form of stress measurement in which the angle between the detectors can be increased from the value $2\pi - 4\theta m$ used in the single exposure technique described so far to a larger operating value. For this purpose the diffraction lines are measured sequentially in the respective detectors. The result is a technique that has the benefit of the double exposure technique, i.e. an increased angle between the two detector positions, without the disadvantage of the double exposure technique, namely the need for the whole instrument to be reoriented between the two strain measurements. This alternative procedure can thus increase the accuracy of stress determination in cases where the back reflection angle $\pi - 2\theta m$ of the chosen reflection is small and the strain directions in the specimen are consequently close together. Increasing the interdetector angle increases the factor K1-K2 in equation 1 and increases the magnitude of the measured strain difference, giving a lower resultant error in the surface stress component $\sigma_n$.

Calibration

The detectors can be calibrated with a standard specimen of known lattice spacing, to give the $2\theta$ value for each channel by means of the source scan. Such a standard specimen should be strain free and can be any material that has a well known lattice spacing and gives a diffraction line in the required region. Generally this material is chosen to be made of the basic element in the stressed specimen under examination, providing it has the same crystal structure as the stressed material. For example, if the stressed specimen is ferritic steel, the standard specimen can be iron. The lattice spacing of the standard specimen does not have to be the same as that of a strain free sample of the stressed material.

The standard specimen gives the diffraction angle $2\theta m$ for the peak channel, using the known standard lattice spacing d and the wavelength peak value $\lambda m$ in Bragg's relation, equation 2. This is sufficient to determine the $2\theta$ value of one channel. Initially, the detector output has been sorted in channels by the multichannel analyser or computer, the angular displacement between detector channels being unknown. The scanning X-ray tube can be used with the standard specimen to determine the mean channel width by scanning the X-ray tube through a known angle and measuring the peak channel of the standard specimen a second time. Knowledge of the value of $2\theta$ for the reference channel and the mean channel width enables the $2\theta$ value of each channel to be determined.

Alternative Construction

In the embodiment of the invention shown in FIG. 6, the source F is scanned relative to the specimen, while the detector or detectors are fixed relative to the source. While scanning of the source is essential to the invention, the fixing of the detectors is not. There is thus an alternative construction available in which the detectors are fixed to the source and the whole assembly is scanned relative to the specimen.

In this case, since the position sensitive detector (or detectors) is an open counter, rotation of each detector will shift the pattern due to the source scan through an angle $-\omega$ in the detector.

The detector equation 9A then becomes $$2\theta = 2\theta_0 + \alpha \qquad (18A)$$

The equation 9B for the relation of the specimen diffraction direction to the diffraction angle is unchanged. Combining equation 9B and 18A gives $$\gamma = \alpha/2 + \omega \qquad (18B)$$

The reference diffraction angle $2\theta_0$ remains at Xo for all rotation angles. The position Xr for strain direction Hr in the detector is at an angle $-2\omega$ to Xo. The displacement Xr is therefore twice that for the first example with a fixed detector, and the effective detector range is one half that for the first example.

The detector position X for any given $2\theta$ value remains fixed during the scan, while the diffraction direction changes. Oscillation of the assembly through a range of $\omega$ values will result in an automatic summation of intensities for each $2\theta$ value. The resultant diffraction line will have an increased specimen diffracting volume, but the range of specimen directions will be different for each $2\theta$ value. Scanning to obtain diffraction by a limited range of directions equidistant about Hr can be carried out in a similar analysis to that used for the first example.

Looking at this result pictorially in relation to FIG. 8, the effect will be that the intensity values for a given $2\theta$ value will lie along a vertical line, i.e. will remain in the same channel throughout. The window G will move to the left at twice the rate of that in FIG. 8, i.e. two channels per scan and the second increment of window movement relative to the reference diffraction angle value will be equal to the first increment of movement relative to the reference channel position.

I claim:

1. In a method of obtaining a diffraction line intensity distribution in a surface area of a polycrystalline specimen by X-ray diffraction including
   (a) projecting an X-ray beam onto said area,
   (b) receiving in a position sensitive detector X-rays diffracted by crystal lattice planes in said area,
   (c) converting the X-rays received in said detector into a diffraction array of intensity values as a function of diffraction angle,
   (d) step scanning the projected beam angularly about said area to generate a sequence of said arrays, said step scanning being such that the angle between said X-ray beam and a normal to said area changes with each step relative to the angle between the centre of width of the detector and said normal, and
   (e) averaging the intensity values of said arrays for each of a series of said diffraction angles;
   the improvement comprising
   (f) restricting the intensity values so averaged to those obtained from a virtual window in the detector that is such that the centre of width of the window is coincident with the diffracted beam received from a set of said lattice planes normal to a chosen direction, and
   (g) displacing said virtual window relative to said diffraction array for each successive scanning position to obtain a resultant diffraction line intensity distribution.

2. The method of claim 1, including determining from said resultant diffraction line intensity distribution derived in step (g) the diffraction angle corresponding to the location of a preselected characteristic of said resultant diffraction line intensity distribution as a measure of a first strain lying in said chosen direction.

3. The method of claim 2, wherein said conversion step (c) comprises
   (h) first converting the X-rays received in the detector into a preliminary array of intensity values as a function of channel position in the detector, and
   (i) then converting said preliminary array into said diffraction array.

4. The method of claim 3, wherein said window is displaced for each successive scanning position by a first increment relative to a reference channel position and by a second increment relative to a reference diffraction angle value in the diffraction array.

5. The method of claim 4, including
   (j) maintaining said detector fixed relative to the specimen, and
   (k) setting said second increment equal to twice said first increment.

6. The method of claim 4, including
   (j) maintaining said detector fixed relative to said projected X-ray beam, and
   (k) setting said first and second increments equal to each other.

7. The method of claim 1 or 2, wherein said projected beam is scanned through a width at least equal to the sum of the width of the diffraction line intensity distribution and the width of an expected maximum displacement of the diffraction line.

8. The method of claim 7, wherein the width of the window lies in a range extending from an upper value approximately equal to the width through which said projected beam is scanned to a lower value approximately equal to the combined width of instrumental broadening and lattice deformation distributions.

9. The method of claim 2, including
   (h) simultaneously with said receiving step (b), receiving in a second position sensitive detector located on the opposite side of the projected beam from the first detector, X-rays diffracted by a second set of crystal lattice planes in said area normal to a second chosen direction,
   (i) converting the X-rays received in said second detector into a second diffraction array of intensity values as a function of diffraction angle, said step scanning of the projected beam generating a second sequence of said second diffraction arrays,
   (j) averaging the intensity values of said second diffraction array for each of a series of said diffraction angles, while restricting the intensity values so averaged to those obtained from a second virtual window in the second detector that is such that the centre of width of the second window is conincident with the diffracted beam received from said second set of lattice planes, while displacing said second virtual window relative to said second diffraction array for each successive scanning position to obtain a second resultant diffraction line intensity distribution,
   (k) determining from said second resultant diffraction line intensity distribution the diffraction angle corresponding to tha location of a preselected characteristic of said second resultant diffraction line intensity distribution as a measure of a second strain lying in said second chosen direction, and
   (l) calculating the normal stress component in the specimen from said first and second strains.

10. The method of claim 2, including
    (h) subsequent to said receiving step (b), moving said detector to a second location corresponding to a second chosen direction and receiving in said detector in the second location, X-rays diffracted by a second set of crystal lattice planes in said area,
    (i) converting the X-rays received in said detector in the second location into a second diffraction array of intensity values as a function of diffraction angle,
    (j) step scanning the projected beam relative to said area to generate a second sequence of said second diffraction arrays,
    (k) averaging the intensity values of said second diffraction array for each of a series of said diffraction angles, while restricting the intensity values so averaged to those obtained from a second virtual window in the detector that is such that the centre of width of the second virtual window is coincident with the diffracted beam received from said second set of lattice planes normal to said second chosen direction, while displacing said second virtual window relative to said second diffraction array for each successive scanning position to obtain a second resultant diffraction line intensity distribution,
    (l) determining from said second resultant diffraction line intensity distribution the diffraction angle corresponding to the location of a preselected characteristic of said second resultant diffraction line intensity distribution as a measure of a second strain lying in said second chosen direction, and
    (m) calculating the normal stress component in the specimen from said first and second strains.

11. The method of claim 2, including
    (h) locating a second position sensitive detector on the opposite side of the projected beam from the first detector with the angle subtended by the two detectors at the specimen area greater than twice the back reflection angle defined at the specimen area between the projected beam and the beam diffracted to the first detector, (i) converting the X-rays received in said second detector into a second diffraction array of intensity values as a function of diffraction angle, (j) subsequent to said step scanning of the projected beam in step (d), step scanning the projected beam angularly about said area to generate a second sequence of said second diffraction arrays, (k) averaging the intensity values of said second diffraction array for each of a series of said diffraction angles, while restricting the intensity values so averaged to those obtained from a second virtual window in the second detector that is such that the centre of width of the second window is coincident with the diffracted beam received from a second set of lattice planes normal to a second chosen direction, while displacing said second virtual window relative to said second diffraction array for each successive scanning position to obtain a second resultant diffraction line intensity distribution, (l) determining from said second resultant diffraction line intensity distribution the diffraction angle corresponding to the location of a preselected characteristic of said second resultant diffraction line intensity distribution as a measure of a second strain lying in said second chosen direction, and (m) calculating the normal stress component in the specimen from said first and second strains.

12. In X-ray diffractometer apparatus for obtaining a diffraction line intensity distribution in a chosen surface area of a polycrystalline specimen, comprising (a) an X-ray source for generating an X-ray beam collimated to a small area, (b) a position sensitive detector, (c) mounting means for the source and the detector, whereby, upon locating said mounting means in a fixed position relative to the speciment with said area irradiated by said beam, the detector will receiv X-rays diffracted by crystal lattice planes in said area, (d) processing means connected to the detector for converting the X-rays received in said detector into a diffraction array of intensity values as a function of diffraction angle, (e) said mounting means including means for step scanning the source relative to the specimen to generate in said processing means a sequence of said arrays, said step scanning being such that the angle between said X-ray beam and a normal to said area changes with each step relative to the angle between the center of width of the detector and said normal, and (f) said processing means averaging the intensity values of said sequence of arrays for each of a series of said diffraction angles, the improvement wherein said processing means includes (g) means for restricting the intensity values so averaged to those obtained from a virtual window in the detector that is such that the centre of width of the window is coincident with the diffracted beam received from a set of said lattice planes normal to a chosen direction, and for displacing said virtual window relative to said diffraction array for each successive scanning position to obtain a resultant diffraction line intensity distribution.

13. The apparatus of claim 12, wherein said processing means includes means for determining from said resultant diffraction line intensity distribution the diffraction angle corresponding to the location of a preselected characteristic of said resultant diffraction line intensity distribution as a measure of a first strain lying in said chosen direction.

14. The apparatus of claim 13, wherein said processing means comprises (h) means for converting the X-rays received in the detector into a preliminary array of intensity values as a function of channel position in the detector, and (i) means for converting said preliminary array into said diffraction array.

15. The apparatus of claim 14, wherein said means for displacing said window is such as to displace said window for each successive scanning position by a first increment relative to a reference channel position and by a second increment relative to a reference diffraction angle value in the diffraction array.

16. The apparatus of claim 15, wherein (j) said mounting means includes means for securing said detector in a fixed position on said mounting means and hence in a fixed position relative to the specimen, and (k) said second increment is equal to twice said first increment.

17. The apparatus of claim 15, wherein (j) said mounting means includes means for securing said detector to said source for step scanning therewith, and (k) said first and second increments are equal to each other.

18. The apparatus of claim 13, including (h) a second position sensitive detector, (i) said mounting means including means for mounting said second detector on the opposite side of the projected beam from the first detector to receive X-rays diffracted by a second set of crystal lattice planes in said area normal to a second chosen direction, (j) said processing means including means for converting the X-rays received in said second detector into a second diffraction array of intensity values as a function of diffraction angle, said means for step scanning the source generating a second sequence of said second diffraction arrays, (k) said processing means including means for averaging the intensity values of said second diffraction array for each of a series of said diffraction angles, while restricting the intensity values so averaged to those obtained from a second virtual window in the second detector that is such that the centre of width of the second virtual window is coincident with the diffracted beam received from the second set of lattice planes, and for displacing said second virtual window relative to said second diffraction array for each successive scanning position to obtain a second resultant diffraction line intensity distribution, and means for determining from said second resultant diffraction line intensity distribution the diffraction angle corresponding to the location of a preselected characteristic of said second resultant diffraction line intensity distribution as a measure of a second strain lying in said second chosen direction, and means for calculating the normal stress component in the specimen from said first and second strains.

19. The apparatus of claim 18, wherein said processing means includes means for calculating the normal stress component in the specimen from two strains measured by said diffraction angle determining means with the detector positioned at different locations on said mounting means relative to the source.

* * * * *